(12) United States Patent
Stanley

(10) Patent No.: US 6,613,527 B1
(45) Date of Patent: *Sep. 2, 2003

(54) ELECTROCHEMICAL DENATURATION OF DOUBLE-STRANDED NUCLEIC ACID

(75) Inventor: Christopher J. Stanley, Huntingdon (GB)

(73) Assignee: Affymetrix, Inc., Santa Clara, CA (US)

(*) Notice: Subject to any disclaimer, the term of this patent is extended or adjusted under 35 U.S.C. 154(b) by 36 days.

This patent is subject to a terminal disclaimer.

(21) Appl. No.: 10/122,139

(22) Filed: Apr. 15, 2002

Related U.S. Application Data

(63) Continuation of application No. 09/568,622, filed on May 10, 2000, now Pat. No. 6,395,489, which is a continuation of application No. 09/127,115, filed on Jul. 31, 1998, now Pat. No. 6,197,508, which is a continuation of application No. 08/617,675, filed on Apr. 1, 1996, now Pat. No. 5,824,477, which is a continuation-in-part of application No. 08/288,231, filed on Aug. 9, 1994, now Pat. No. 5,527,670, which is a continuation of application No. 08/030,138, filed on Mar. 12, 1993, now abandoned, which is a continuation of application No. PCT/GB91/01563, filed on Sep. 12, 1991, now abandoned.

(30) Foreign Application Priority Data

Sep. 12, 1990 (GB) .............................. 9019946
Jun. 14, 1991 (GB) .............................. 9112911

(51) Int. Cl.$^7$ .......................... C12Q 1/68; G01N 33/00
(52) U.S. Cl. .............................. 435/6; 436/94
(58) Field of Search ................... 435/6; 436/94

(56) References Cited

U.S. PATENT DOCUMENTS

| | | | |
|---|---|---|---|
| 4,683,202 A | 7/1987 | Mullis | |
| 4,787,963 A | 11/1988 | MacConnell | |
| 4,945,045 A | 7/1990 | Forrest et al. | |
| 5,527,670 A | 6/1996 | Stanley | |
| 5,565,322 A | 10/1996 | Heller | 435/6 |
| 5,605,662 A | 2/1997 | Heller et al. | 422/68 |
| 5,607,832 A | 3/1997 | Stanley et al. | |
| 5,632,957 A | 5/1997 | Heller et al. | 422/68 |
| 5,824,477 A | 10/1998 | Stanley | 435/6 |
| 5,849,486 A | 12/1998 | Heller et al. | 435/6 |
| 5,849,489 A | 12/1998 | Heller | 435/6 |
| 5,869,244 A | 2/1999 | Martin et al. | 435/6 |
| 5,965,452 A | 10/1999 | Kovacs | 436/149 |
| 6,013,166 A | 1/2000 | Heller | 204/469 |
| 6,017,696 A | 1/2000 | Heller | 435/6 |
| 6,033,850 A | 3/2000 | Purvis | 435/6 |
| 6,051,380 A | 4/2000 | Sosnowski et al. | 435/6 |
| 6,071,394 A | 6/2000 | Cheng et al. | 204/547 |
| 6,129,828 A | 10/2000 | Sheldon, III et al. | 204/518 |
| 6,150,106 A | 11/2000 | Martin et al. | 435/6 |
| 6,162,603 A | 12/2000 | Heller | 435/6 |
| 6,197,508 B1 | 3/2001 | Stanley | 435/6 |
| 6,395,489 B1 | 5/2002 | Stanley | 435/6 |

FOREIGN PATENT DOCUMENTS

| | | |
|---|---|---|
| EP | 0201184 | 3/1986 |
| EP | 0320308 | 12/1998 |
| WO | 92/04470 | 3/1992 |
| WO | 97/15224 | 8/1993 |
| WO | 97/08293 | 3/1997 |
| WO | 97/41219 | 11/1997 |
| WO | 97/43445 | 11/1997 |

OTHER PUBLICATIONS

Berg, Polarographic Possibilities in Protein and Nucleic Acid Research, 3 sup.rd Intl. Symp. held at Julich (1975), pp. 40–104

Boublikova et al., *Studia Biophysica*, vol. 114 (1986), pp. 83–90.

Brabec et al., *Biophysical Chemistry*, vol. 4 (1976), pp. 79–92.

Brabec,et al., *J. Electroanal. Chem.* vol. 88 (1978), pp. 373–385.

Brabec,et al., *Bioelectrochemistry & Bioenergetics*, vol. 8 (1981), pp. 437–449.

Brabec,et al., *Bioelectrochemistry & Bioenergetics*, vol. 11 (1983), pp. 245–255.

Brabec,et al., *Biophysical Chemistry*, vol. 23 (1985), pp. 63–70.

Eddows et al., *J.C.S. Chem. Commun.* (1977), pp. 771–772.

Fultz et al., Analytica Chimica Acta, vol. 140 (1982), pp. 1–16.

Jelen & Palcek, *General Physiology & Biophysics*, vol. 4 (1985), pp. 219–237.

Jelen et al., *Biophysical Chemistry*, vol. 24 (1986), pp. 285–290.

Nurnberg, Applications of Advanced Voltammetric Methods in Bioelectrochemistry, pp. 183–225.

Palecek et al., *Collection Czech. Chem. Commun.* vol. 44 (1979), pp. 448–455.

Palecek, *Topics in Bioelectrochemistry & Bioenergetics*, vol. 5 (1983), pp. 65–155.

Palecek, *Bioelectrochemistry & Bioenergetics*, vol. 15 (1986), pp. 275–295.

(List continued on next page.)

*Primary Examiner*—Kenneth R. Horlick
(74) *Attorney, Agent, or Firm*—Morgan, Lewis & Bockius LLP

(57) ABSTRACT

A process is described for denaturing native double-stranded nucleic acid material into its individual strands in an electrochemical cell. The process disclosed is an electrical treatment of the nucleic acid with a voltage applied to the nucleic acid material by an electrode. The process may also employ a promoter compound such as methyl viologen to speed denaturation. The process may be used in the detection of nucleic acid by hybridizing with a labelled probe or in the amplification of DNA by a polymerase chain reaction or ligase chain reaction.

23 Claims, 6 Drawing Sheets

OTHER PUBLICATIONS

Palecek et al., *Analytica Chimica Acta*, vol. 187 (1986), pp. 99–107.

Palecek, *Analytical Biochemistry*, vol. 170 (1988), pp. 421–431.

Palecek, *Bioelectrochemistry & Bioenergetics*, vol. 20 (1988), pp. 179–194.

Palecek et al., *Bioelectrochemistry & Bioenergetics*, vol. 23 (1990), pp. 285–299.

Palecek, *Bioelectrochemistry & Bioenergetics*, vol. 28 (1992), pp. 71–83.

Pawlowski et al., *Acta Biochimica Polpnica*, vol. 36 (1989), pp. 75–85.

Stanley et al., *J. Immunol. Methods*, vol. 112 (1988), pp. 153–161.

Valenta et al., *Biophys. Struct. Mechanism*, vol. 1 (1974) pp. 17–26.

Walker et al., *J. Am. Chem. Society*, vol. 110 (1988), pp. 6234–6240.

double stranded M13 single stranded M13 d,s DNA s,s DNA

ELECTROCHEMICAL DENATURATION OF DOUBLE-STRANDED NUCLEIC ACID

CROSS-REFERENCE TO RELATED APPLICATIONS

This application is a continuation of application Ser. No. 09/568,622, filed May 10, 2000 U.S. Pat. No. 6,395,489; which is a continuation of application Ser. No. 09/127,115, filed Jul. 31, 1998, now U.S. Pat. No. 6,197,508; which is a continuation of application Ser. No. 08/617,675, filed Apr, 1, 1996, now U.S. Pat. No. 5,824,477; which is a continuation-in-part of application Ser. No. 08/288,231, filed Aug. 9, 1994, now U.S. Pat. No. 5,527,670; which is a continuation of application Ser. No. 08/030,139, filed Mar. 12, 1993, now abandoned, which is a continuation of PCT/GB91/01563, filed Sep. 12, 1991, the disclosure of each of which is incorporated herein by reference in its entirety for all purposes. This application also claims the priority dates of Sep. 12, 1990 and Jun. 14, 1991, the filing dates of the corresponding United Kingdom patent applications 9019946.4 and 9112911.4, respectively, the disclosure of each of which is incorporated herein by reference in its entirety for all purposes.

BACKGROUND OF THE INVENTION

1. Field of the Invention

This invention relates to processes for the treatment of nucleic acid material in order to effect a complete or partial change from double-stranded form to single-stranded form and to processes of amplifying or detecting nucleic acids involving such denaturation processes.

Double-stranded DNA (deoxyribonucleic acid) and DNA/RNA (ribonucleic acid) and RNA/RNA complexes in the familiar double helical configuration are stable molecules that, in vitro, require aggressive conditions to separate the complementary strands of the nucleic acid. Known methods that are commonly employed for strand separation require the use of high temperatures of at least 60° Celsius and often 100° C. for extended periods of ten minutes or more or use an alkaline pH of 11 or higher. Other methods include the use of helicase enzymes, such as Rep protein of E. coli, that can catalyze the unwinding of the DNA in an unknown way, or binding proteins such as 32-protein of E. coli phage T4 that act to stabilize the single-stranded form of DNA. The denatured single-stranded DNA produced by the known processes of heat or alkali is used commonly for hybridization studies or is subjected to amplification cycles.

2. Description of the Prior Art

U.S. Pat. No. 4,683,202 (Mullis et al., assigned to Cetus Corporation) discloses a process for amplifying and detecting a target nucleic acid sequence contained in a nucleic acid or mixture thereof by separating the complementary strands of the nucleic acid, hybridizing with specific oligonucleotide primers, extending the primers with a polymerase to form complementary primer extension products and then using those extension products for the further synthesis of the desired nucleic acid sequence by allowing hybridization with the specific oligonucleotide primers to take place again. The process can be carried out repetitively to generate large quantities of the required nucleic acid sequence from even a single molecule of the starting material. Separation of the complementary strands of the nucleic acid is achieved preferably by thermal denaturation in successive cycles, since only the thermal process offers simple reversibility of the denaturation process to reform the double-stranded nucleic acid, in order to continue the amplification cycle.

However, the need for thermal cycling of the reaction mixture limits the speed at which the multiplication process can be carried out, owing to the slowness of typical heating and cooling systems. It also requires the use of special heat resistant polymerase enzymes from thermophilic organisms for the primer extension step, if the continuous addition of heat labile enzyme is to be avoided. It limits the design of new diagnostic formats that use the amplification process because heat is difficult to apply in selective regions of a diagnostic device and it also can be destructive to the structure of the DNA itself because the phosphodiester bonds may be broken at high temperatures leading to a collection of broken single strands. It is generally believed that the thermophilic polymerases in use today have a lower fidelity, i.e., make more errors in copying DNA, than do enzymes from mesophiles. It is also the case that thermophilic enzymes, such as TAQ polymerase have a lower turnover number than heat labile enzymes, such as the Klenow polymerase from E. coli. In addition, the need to heat to high temperatures, usually 90° C. or higher to denature the nucleic acid leads to complications when small volumes are used as the evaporation of the liquid is difficult to control. These limitations have so far placed some restrictions on the use of the Mullis et al. process in applications requiring very low reagent volumes to provide reagent economy, in applications where the greatest accuracy of copy is required, such as in the Human Genome sequencing project and in the routine diagnostics industry where reagent economy, the design of the assay format and the speed of the DNA denaturation/renaturation process are important.

Denaturation/renaturation cycles are also required in order to perform the so-called ligase chain reaction described in EP-A-0320308, in which amplification is obtained by ligation of primers hybridized to template sequences, rather than by extending them.

It is known that DNA has electrochemical properties. For example, N. L. Palacek, in "Electrochemical Behaviour of Biological Macromolecules," *Bioelectrochemistry and Bioenergetics*, 15 (1986), pp. 275–295, discloses the electrochemical reduction of adenine and cytosine in thermally denatured single-stranded DNA at about −(minus) 1.5 V. on the surface of a mercury electrode. This reduction process also requires a prior protonation and therefore takes place at a pH below 7.0. The primary reduction sites of adenine and cytosine form part of the hydrogen bonds in the Watson-Crick base pairs. Palacek was unable to demonstrate reduction of adenine and cytosine in intact, native double-stranded DNA at the mercury electrode. Palacek has further demonstrated that, to a very limited extent, the DNA double helix is opened on the surface of the mercury electrode at a narrow range of potentials centered at −(minus) 1.2 V. in a slow process involving an appreciable part of the DNA molecule. This change in the helical structure of the DNA is thought to be due to prolonged interaction with the electrode charged to certain potentials and is not thought to be a process involving electron transfer to the DNA. No accumulation of single-stranded DNA in the working solution was obtained and no practical utility for the phenomenon was suggested. Palacek also reports that the guanine residues in DNA can be reduced at −(minus) 1.8 V. to dihydroguanine which can be oxidized back to guanine at around −(minus) 0.3 V. The reducible guanine double bond is not part of the hydrogen bonds in the Watson-Crick base pairs and this electrochemical process involving guanine does not affect the structure of the DNA double helix.

In an earlier paper, F. Jelen and E. Palacek ("Nucleotide Sequence-Dependent Opening of Double-Stranded DNA at an Electrically Charged Surface," *Gen. Physiol. Biophys.*, 4 (1985), pp. 219–237), describe in more detail the opening of the DNA double helix on prolonged contact of the DNA molecules with the surface of a mercury electrode. The mechanism of opening of the helix is postulated to be anchoring of the polynucleotide chain via the hydrophobic bases to the electrode surface after which the negatively charged phosphate residues of the DNA are strongly repelled from the electrode surface at an applied potential close to −(minus) 1.2 V, the strand separation being brought about as a result of the electric field provided by the cathode. There is no disclosure of separating the strands of the DNA double helix while the DNA is in solution (rather than adsorbed onto the electrode) and there is no disclosure of useful amounts of single strand DNA in solution. Furthermore, there is no disclosure that the nucleotide base sequence of the DNA on the electrode is accessible from solution. The bases themselves are tightly bound to the mercury surface. A mercury electrode is a complex system and the electrode can only be operated in the research laboratory with trained technical staff.

H. W. Nurnberg, in "Applications of Advanced Voltammetric Methods in Electrochemistry," *Bioelectrochemistry*, Plenum Inc. (New York), 1983, pp. 183–225, discloses partial helix opening of adsorbed regions of native DNA to a mercury electrode surface to form a so-called ladder structure. However, the DNA is effectively inseparably bound to or adsorbed onto the electrode surface. In this condition, it is believed that the denatured DNA is of no use for any subsequent process of amplification or hybridization analysis. To be of any use, the denatured DNA must be accessible to subsequent processes and this is conveniently achieved if the single-stranded DNA is available in free solution or is associated with the electrode in some way but remains accessible to further processes. Nurnberg has not demonstrated the ability of the mercury electrode to provide useful quantities of single-stranded DNA.

V. Brabec and K. Niki ("Raman scattering from nucleic acids adsorbed at a silver electrode" in *Biophysical Chemistry*, 23 (1985), pp. 63–70) have provided a useful summary of the differing views from several workers on DNA denaturation at the surface of both mercury and graphite electrodes charged to negative potentials. There has emerged a consensus amongst the research workers in this field that the denaturation process only takes place in DNA that is strongly adsorbed to the electrode surface and only over prolonged periods of treatment with the appropriate negative voltage, a positive voltage having no effect on the double helix.

Brabec and Palacek (*J. Electroanal. Chem.*, 88 (1978), pp. 373–385) disclose that sonicated DNA damaged by gamma radiation is transiently partially denatured on the surface of a mercury pool electrode, the process being detectable by reacting the single-stranded products with formaldehyde so as to accumulate methylated DNA products in solution. Intact DNA did not show any observable denaturation.

SUMMARY OF THE INVENTION

The present invention provides a process for denaturing double-stranded nucleic acid which comprises operating on solution containing nucleic acid with an electrode under conditions such as to convert a substantial portion of said nucleic acid to a wholly or partially single-stranded form.

It has been found that it is possible to produce the denaturation of undamaged, i.e., non-irradiated, DNA at ambient temperature by applying a suitable voltage to a solution in which the DNA is present under suitable conditions.

The mechanism for the process has not yet been fully elucidated. It is believed that the process is one in which the electric field at the electrode surface produces the denaturation of the double helix when the DNA is in close proximity to the electrode, but not bound irreversibly to it.

The process is found to be readily reversible. In polymerase chain reaction processes exemplified hereafter, it is shown that the denatured DNA produced by the denaturing process of the invention is immediately in a suitable state for primer hybridization and extension. On a larger scale, it is found that samples of denatured DNA produced using a negative voltage electrode can be caused or encouraged to renature by reversal of the voltage or by incubation at a higher temperature to encourage reannealing.

Preferably, according to the invention, the single-stranded nucleic acid produced is free from the electrode, e.g., in solution. However, the nucleic acid may be immobilized on the electrode in double or single-stranded form prior to the application of the electrode potential, e.g., attached by the end or a small portion intermediate the ends of the nucleic acid chain, so as to leave substantial segments of the nucleic acid molecules freely pendant from the electrode surface before and after denaturation.

Preferably, a potential of from −0.2 to −3 V, (more preferably from −0.5 to −1.5 V) is applied to said working electrode with respect to the solution. More preferably still, the voltage is from −0.8 to −1.1 V, e.g., about −1.0 V.

Working electrode voltages are given throughout as if measured or as actually measured relative to a calomel reference electrode (BDH No. 309.1030.02).

In addition to said electrode and a counter-electrode, a reference electrode may be contacted with said solution and a voltage may be applied between said electrode and said counter-electrode so as to achieve a desired controlled voltage between said electrode and said reference electrode. The electrodes may be connected by a potentiostat circuit as is known in the electrochemical art.

The ionic strength of said solution is preferably no more than 250 mM, more preferably no more than 100 mM. As it has been found that the rate of denaturation increases as the ionic strength is decreased, the said ionic strength is still more preferably no more than 50 mM, e.g., no more than 25 mM or even no more than 5 mM. Generally, the lower the ionic strength, the more rapid is the denaturation. However, in calculating ionic strength for these purposes it may be appropriate to ignore the contribution to ionic strength of any component which acts as a promoter as described below.

The solution may contain or the electrode may have on its surface a promoter compound which assists said denaturation.

Although the invented process can take place in a solution containing only the electrode and the nucleic acid dissolved in water optionally containing a suitable buffer, the process can be facilitated by the presence in the solution containing the nucleic acid of such a promoter compound.

The compound may act as a promoter serving either to destabilize the double-stranded nucleic acid, for instance by intercalation into the double helix, or to stabilize the single-stranded form, or else to facilitate interaction between the electrode surface and the nucleic acid. By way of analogy, it has been found that 4,4'-bipyridyl promotes the reduction of cytochrome C at a gold electrode, even though bipyridyl is, in itself, electroinactive at the voltages used. (M. J. Eddowes and H. A. Hill, *J. Chem. Soc. Chem. Commun.* (1977), 771.)

The promoter may be any inorganic or organic molecule which increases the rate or extent of denaturation of the DNA double helix. It should be soluble in the chosen solvent. It preferably does not affect or interfere with DNA or other materials (such as enzymes or oligonucleotide probes) which may be present in the solution. Alternatively, the promoter may be immobilized to or included in the material from which the electrode is constructed.

In experiments, it has been found that the promoter may be a water soluble compound of the bipyridyl series, especially a viologen such as methyl viologen or a salt thereof.

It is believed that the positively-charged viologen molecules interact between the negatively-charged DNA and the negatively-charged cathode to reduce electrostatic repulsion therebetween and, hence, to promote the approach of the DNA to the electrode surface where the electrical field is at its strongest. Accordingly, we prefer to employ as promoter compounds having spaced positively charged centers, e.g., bipolar positively charged compounds. Preferably, the spacing between the positively charged centers is similar to that in viologens. Other suitable viologens include ethyl viologen, isopropyl viologen and benzyl viologen.

The process may be carried out in an electrochemical cell of the type described by C. J. Stanley, M. Cardosi and A. P. F. Turner, "Amperometric Enzyme Amplified Immunoassays," *J. Immunol. Meth.*, 112 (1988), pp. 153–161, in which there is a working electrode, a counter electrode and, optionally, a reference electrode. The working electrode at or by which the denaturing nucleic acid is effected may be of any convenient material, e.g., a noble metal such as gold or platinum, or a glassy carbon electrode.

The electrode may be a so-called "modified electrode," in which the denaturing is promoted by a compound coated onto, or adsorbed onto, or incorporated into the structure of the electrode which is otherwise of an inert but conducting material. In an alternative electrochemical cell configuration, the working, counter and reference electrodes may be formed on a single surface, e.g., a flat surface by any printing method such as thick film screen printing, ink jet printing, or by using a photo-resist followed by etching. It is also possible that the working and reference electrodes can be combined on the flat surface leading to a two-electrode configuration where the reference also acts as the counter. Alternatively, the electrodes may be formed on the inside surface of a well which is adapted to hold liquid. Such a well could be the well-known 96 well or Microtitre plate, it may also be a test tube or other vessel. Electrode arrays in Microtitre plates or other molded or thermoformed plastic materials may be provided for multiple nucleic acid denaturation experiments.

The strand separation may be carried out in an aqueous medium or in a mixture of water with an organic solvent such as dimethylformamide. The use of polar solvents other than water or non-polar solvents is also acceptable, but is not preferred. The process may be carried out at ambient temperatures or, if desired, temperatures up to adjacent the pre-melting temperature of the nucleic acid. The process may be carried out at pHs of from 3 to 10, conveniently about 7. Generally, more rapid denaturation is obtained at lower pH. For some purposes, therefore, a pH somewhat below neutral, e.g., about pH 5.5, may be preferred. The nucleic acid may be dissolved in an aqueous solution containing a buffer whose nature and ionic strength are such as not to interfere with the strand separation process.

The denaturing process according to the invention may be incorporated as a step in a number of more complex processes, e.g., procedures involving the analysis and/or the amplification of nucleic acid. Some examples of such applications are described below.

The invention includes a process for detecting the presence or absence of a predetermined nucleic acid sequence in a sample which comprises: denaturing a sample double-stranded nucleic acid by means of a voltage applied to the sample in a solution by means of an electrode; hybridizing the denatured nucleic acid with an oligonucleotide probe for the sequence; and determining whether the said hybridization has occurred.

Thus, the invented process has application in DNA and RNA hybridization where a specific gene sequence is to be identified, e.g., specific to a particular organism or specific to a particular hereditary disease of which sickle cell anemia is an example. To detect a specific sequence, it is first necessary to prepare a sample of DNA, preferably of purified DNA, means for which are known, which is in native double-stranded form. It is then necessary to convert the double-stranded DNA to single-stranded form before a hybridization step with a labelled nucleotide probe which has a complementary sequence to the DNA sample can take place. The denaturation process of the invention can be used for this purpose in a preferred manner by carrying out the following steps:

denaturing a sample of DNA by applying a voltage by means of an electrode to the sample DNA with optionally a promoter in solution or bound to or part of the structure of the electrode;

hybridizing the denatured DNA with a directly labelled or indirectly labelled nucleotide probe complementary to the sequence of interest; and determining whether the hybridization has occurred, which determination may be by detecting the presence of the probe, the probe being directly radio-labelled, fluorescent labelled, chemiluminescent labelled or enzyme labelled or being an indirectly labelled probe which carries biotin, for example, to which a labelled avidin or avidin-type molecule can be bound later.

In a typical DNA probe assay, it is customary to immobilize the sample DNA to a membrane surface which may be composed of neutral or charged nylon or nitrocellulose. The immobilization is achieved by charge interactions or by baking the membrane-containing DNA in an oven. The sample DNA can be heated to high temperature to ensure conversion to single-stranded form before binding to the membrane or it can be treated with alkali once on the membrane to ensure conversion to the single-stranded form. The disadvantages of the present methods are:

heating to high temperatures to create single-stranded DNA can cause damage to the sample DNA itself; and the use of alkali requires an additional step of neutralization before hybridization with the labelled probe can take place.

One improved method for carrying out DNA probe hybridization assays is the so-called "sandwich" technique where a specific oligonucleotide is immobilized on a surface. The surface having the specific oligonucleotide thereon is then hybridized with a solution containing the target DNA in a single-stranded form, after which a second labelled oligonucleotide is then added which also hybridizes to the target DNA. The surface is then washed to remove unbound labelled oligonucleotide, after which any label which has become bound to target DNA on the surface can be detected later.

This procedure can be simplified by using the denaturing process of the invention to denature the double-stranded DNA into the required single-stranded DNA. The working electrode, counter electrode and optionally a reference electrode and/or a promoter can be incorporated into a test tube or a well in which the DNA probe assay is to be carried out. The DNA sample and oligonucleotide probes can then be added and the voltage applied to denature the DNA. The resulting single-stranded DNA is hybridized with the specific oligonucleotide immobilized on the surface after the remaining stages of a sandwich assay are carried out. All the above steps can take place without a need for high temperatures or addition of alkali reagents as in the conventional process.

The electrochemical denaturation of DNA can be used in the amplification of nucleic acids, e.g., in a polymerase chain reaction or ligase chain reaction amplification procedure. Thus, the present invention provides a process for replicating a nucleic acid which comprises: separating the strands of a sample double-stranded nucleic acid in solution under the influence of an electrical voltage applied to the solution from an electrode; hybridizing the separated strands of the nucleic acid with at least one oligonucleotide primer that hybridizes with at least one of the strands of the denatured nucleic acid; synthesizing an extension product of the or each primer which is sufficiently complementary to the respective strand of the nucleic acid to hybridize therewith; and separating the or each extension product from the nucleic acid strand with which it is hybridized to obtain the extension product.

In such a polymerase mediated replication procedure, e.g., a polymerase chain reaction procedure, it may not be necessary in all cases to carry out denaturation to the point of producing wholly single-stranded molecules of nucleic acid. It may be sufficient to produce a sufficient local and/or temporary weakening or separation of the double helix in the primary hybridization site to allow the primer to bind to its target. Once the primer is in position on a first of the target strands, rehybridization of the target strands in the primer region will be prevented and the other target strand may be progressively displaced by extension of the primer or by further temporary weakening or separation processes.

Preferably, the said amplification process further comprises repeating the procedure defined above cyclically, e.g., for more than 10 cycles, e.g., up to 20 or 30 cycles. In the amplification process, the hybridization step is preferably carried out using two primers which are complementary to different strands of the nucleic acid.

The denaturation to obtain the extension products as well as the original denaturing of the target nucleic acid is preferably carried out by applying to the solution of the nucleic acid a voltage from an electrode.

The process may be a standard or classical PCR process for amplifying at least one specific nucleic acid sequence contained in a nucleic acid or a mixture of nucleic acids wherein each nucleic acid consists of two separate complementary strands, of equal or unequal length, which process comprises:

(a) treating the strands with two oligonucleotide primers, for each different specific sequence being applied, under conditions such that for each different sequence being amplified, an extension product of each primer is synthesized which is complementary to each nucleic acid strand, wherein said primers are selected so as to be substantially complementary to different strands of each specific sequence such that the extension product synthesized from one primer, when it is separated from its complement, can serve as a template for synthesis of the extension product of the other primer;

(b) separating the primer extension products from the templates on which they were synthesized to produce single-stranded molecules by applying a voltage from an electrode to the reaction mixture; and (c) treating the single-stranded molecules generated from step (b) with the primers of step (a) under conditions such that a primer extension product is synthesized using each of the single strands produced in step (b) as a template.

Alternatively, the process may be any variant of the classical or standard PCR process, e.g., the so-called "inverted" or "inverse" PCR process or the "anchored" PCR process.

The invention therefore includes an amplification process as described above in which a primer is hybridized to a circular nucleic acid and is extended to form a duplex which is denatured by the denaturing process of the invention, the amplification process optionally being repeated through one or more additional cycles.

More generally, the invention includes a process for amplifying a target sequence of nucleic acid comprising hybridization, amplification and denaturation of nucleic acid, e.g., cycles of hybridizing and denaturing, wherein said denaturation is produced by operating on a solution containing said nucleic acid with an electrode.

The process of the invention is applicable to the ligase chain reaction. Accordingly, the invention includes a process for amplifying a target nucleic acid comprising the steps of:

(a) providing nucleic acid of a sample as single-stranded nucleic acid;

(b) providing in the sample at least four nucleic acid probes wherein: i) the first and second of said probes are primary probes, and the third and fourth of said probes are secondary nucleic acid probes; ii) the first probe is a single strand capable of hybridizing to a first segment of a primary strand of the target nucleic acid; iii) the second probe is a single strand capable of hybridizing to a second segment of said primary strand of the target nucleic acid; iv) the 5' end of the first segment of said primary strand of the target is positioned relative to the 3' end of the second segment of said primary strand of the target to enable joining of the 3' end of the first probe to the 5' end of the second probe, when said probes are hybridized to said primary strand of said target nucleic acid; v) the third probe is capable of hybridizing to the first probe; and vi) the fourth probe is capable of hybridizing to the second probe; and (c) repeatedly or continuously: i) hybridizing said probes with nucleic acid in said sample; ii) ligating hybridized probes to form reorganized fused probe sequences; and iii) denaturing DNA in said sample by applying a voltage from an electrode to the reaction mixture.

In all of the amplification procedures described above, the denaturation of the DNA to allow subsequent hybridization with the primers can be carried out by the application of an appropriate potential to the electrode. The process may be carried out stepwise involving successive cycles of denaturation or renaturation as in the existing thermal methods of PCR and LCR, but it is also possible for it to be carried out continuously since the process of chain extension or ligation by the enzyme and subsequent strand separation by the electrochemical process can continue in the same reaction as nucleic acid molecules in single-stranded form will be free to hybridize with primers once they leave the denaturing influence of the electrode. Thus, provided that the primer will hybridize with the DNA an extension or ligation product will be synthesized. The electrochemical DNA amplification technique can be used analytically to detect and analyze a very small sample of DNA, e.g., a single copy gene in an animal or a single cell of a bacterium.

The invention includes a kit for use in a process of detecting the presence or absence of a predetermined nucleic acid sequence in a sample which kit comprises, an electrode, a counter electrode and optionally a reference electrode, an oligonucleotide probe for said sequence. The probe may be labelled in any of the ways discussed above.

The invention also includes a kit for use in a process of nucleic acid amplification comprising an electrode, a counter electrode and optionally a reference electrode, and at least one primer for use in a PCR procedure, or at least one primer for use in an LCR procedure, and/or polymerase or a ligase, and/or nucleotides suitable for use in a PCR process.

Preferably, such kits include a cell containing the electrodes. Preferably the kits include a suitable buffer for use in the detection or amplification. procedure.

BRIEF DESCRIPTION OF THE DRAWINGS

The invention will now be described with reference to the following drawings and examples.

DETAILED DESCRIPTION OF THE PREFERRED EMBODIMENT

Figure 1:
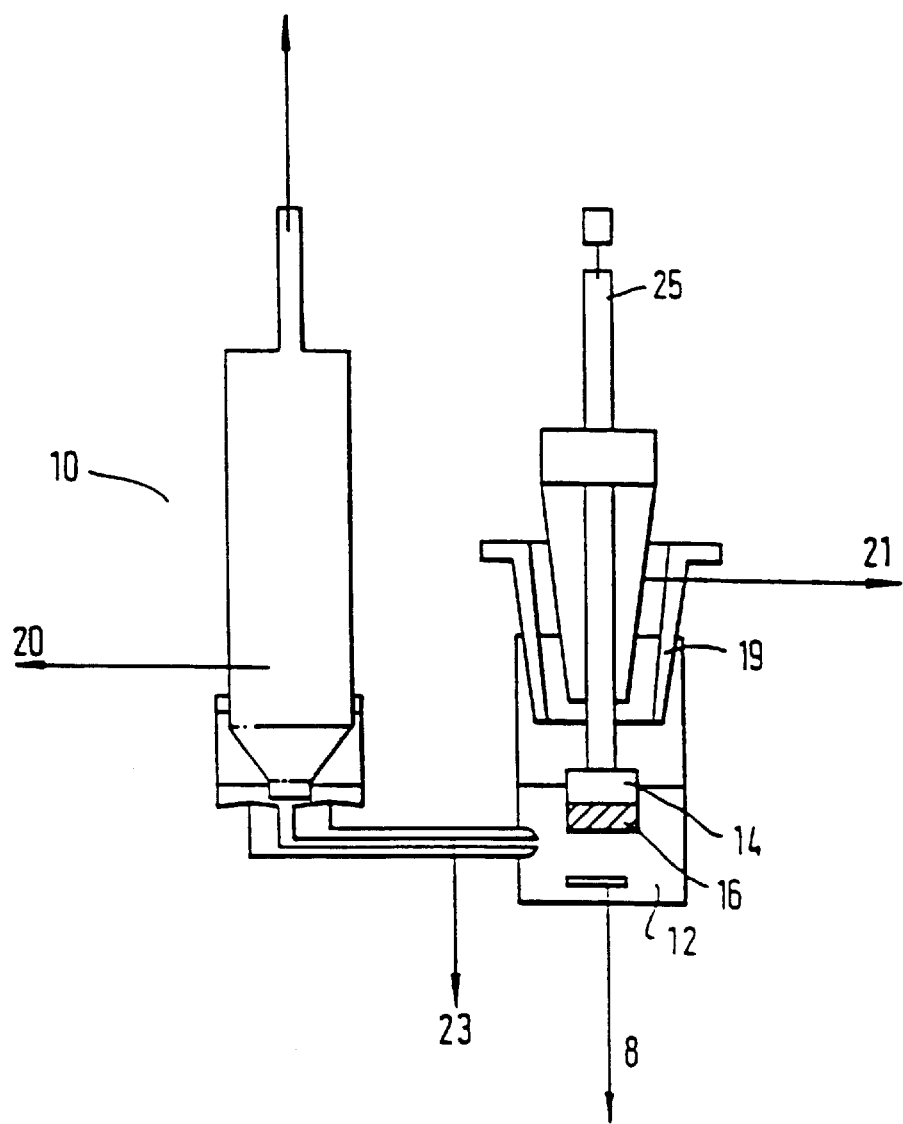
FIG. 1 is a diagram of an electrochemical cell used for denaturation of DNA.

In FIG. 1, there is shown a cell structure 10 comprising a working compartment 12 in which there is a body of DNA-containing solution, a working electrode 14, a counter electrode 16, a FiVac seal 19, a Kwik fit adaptor 21 and magnetic stirrer 18. A reference electrode 20 in a separate side arm is connected via a "luggin" capillary 23 to the solution in the sample 12. The working electrode, counter electrode and reference electrode are connected together in a potentiostat arrangement so that a constant voltage is maintained between the working electrode 14 and the reference electrode 20. Such potentiostat arrangements are well known (see for example "Instrumental Methods in Electrochemistry" by the Southampton Electrochemistry Group, 1985, John Wiley and Sons, p. 19).

The electrode 14 is a circular glassy carbon rod of diameter 0.5 cm, narrowing to 0.25 cm at a height of 10 mM, and having an overall length of 9 cm inside a Teflon™ sleeve of outside diameter 0.8 cm (supplied by Oxford Electrodes, 18 Alexander Place, Abingdon, Oxon), and the reference electrode 16 is a 2 mm pin calomel (supplied by BDH No. 309/1030/02). The counter electrode is supported by a wire which is soldered to a brass sleeve 25 above the adaptor and passes down and exits the Teflon™ sleeve 20 mm from the base the working electrode. The wire attached to a cylindrical platinum mesh counter electrode supplied by Oxford Electrodes which annularly surrounds the working electrode.

EXAMPLE 1

In this example of DNA denaturation, the two methods of thermal and electrical denaturation have been compared. To achieve electrical denaturation, 1.60 ml of solution of methyl viologen dichloride at 1 mg/ml in distilled water (adjusted to pH 7 by titration with 0.1 M sodium hydroxide) was added to the working compartment of the electrochemical cell described above. The reference arm of the cell in which the reference electrode 20 resides contained 0.4 ml of this solution. A sample of 120 $\mu$m of a stock solution of calf thymus DNA (Sigma Chemical Company catalog number: D4522, average fragment size 5,000 bases) at 1 mg/ml in distilled water (the pH was not adjusted) was added to the working chamber of the electrochemical cell to give a 70 $\mu$g/ml final DNA concentration. The total ionic strength of the solution was calculated to be approximate 5 mM. A voltage of –(minus) 1.0 V was applied between the working electrode and the reference electrode.

The electrochemical cell was left for 16 hours at room temperature (22° C.) with continuous gentle stirring. On applying the potential to the working electrode 14, the blue color of reduced methyl viologen was observed in the immediate vicinity of the working electrode. A 100 $\mu$l sample from the working compartment of the electrochemical cell was taken at the end of the experiment and prepared for gel electrophoresis analysis by mixing with 20 $\mu$l of gel loading buffer which was the same as is described below for the gel itself which also contained 0.25% (w/v) bromophenol blue (BDH Indicators 200170), 0.25% (w/v) xylene cyanol (Sigma X2751), and 30% (v/v) glycerol (BDH AnalaR 100118). The mixtures were stored on ice prior to loading 10 $\mu$l samples in the wells cast in an agarose electrophoresis gel.

For the thermal denaturation experiment, the DNA solution at 1 mg/ml in distilled water (the pH was not adjusted) was heated to 100° C. for 10 minutes in a boiling water bath. The tube containing the thermally denatured DNA was then removed from the water bath and placed immediately into a beaker containing an ice/water mix to ensure rapid cooling to prevent renaturation of the sample back to the double-stranded form. A 100 $\mu$l sample of the thermally denatured DNA solution was prepared for gel electrophoresis by mixture with 20 $\mu$l of gel loading buffer which contained 0.25% (w/v) bromophenol blue, 0.25% (w/v) xylene cyanol and 30% (w/v) glycerol.

Native intact calf thymus DNA was also prepared for gel electrophoresis by mixing 100 $\mu$l of the starting solution of DNA (before thermal or denaturation) with 20 $\mu$l of gel loading buffer and stored on ice until required.

Figure 2:
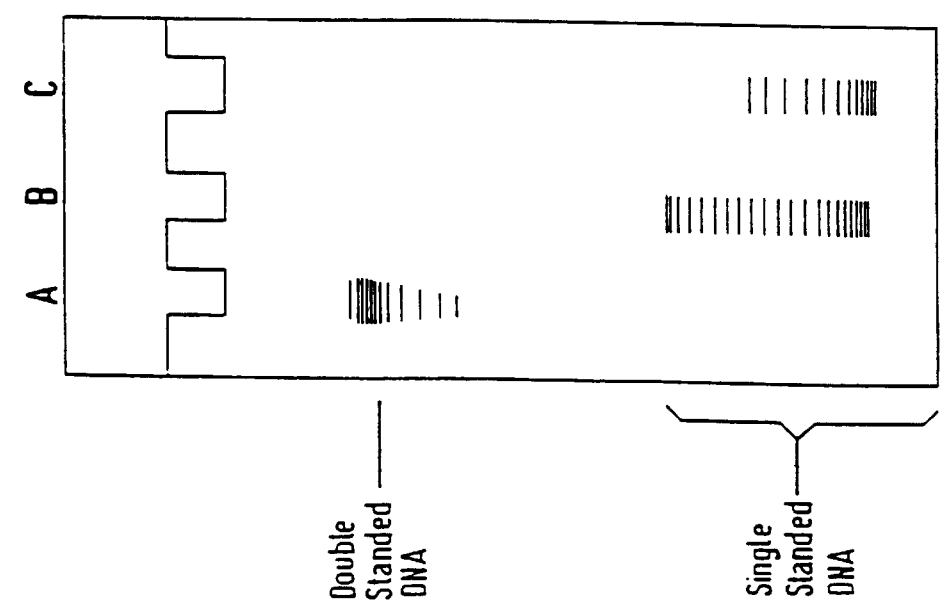
FIG. 2 is a drawing of an electrophoresis gel showing the movement of single and double-stranded DNA.

The gel (a section of which is shown in FIG. 2) had a number of wells 30 into which the samples could be loaded, and 10 μl samples were placed into individual wells. The gel had a total volume of 50 ml and was 10 cm wide and 75 cm long; it was 0.5% (w/v) agarose in 0.089 M tris buffer pH 8.0 containing 0.1 M borate and 0.01 M sodium EDTA. The gel was run for 85 minutes at an applied constant voltage of 55 volts using a power supply from to Pharmacia No. 500/400. The gel was then removed from the electrophoresis apparatus and stained by addition of 0.75 M of ethidium bromide (Pharmacia No. 1840-501, lot 9503860E) at 20 μg/ml in distilled water. After staining for 30 minutes, the gel was washed in distilled water. The stained gel was transilluminated with ultraviolet light and then photographed with a Polaroid® instant camera system using a red filter to reduce background from the UV source.

The gel shown in FIG. 1 has samples A, B and C. Sample A was the starting material used in the test (calf thymus DNA). Sample B was a sample of calf thymus DNA which had been electrically denatured according to the invention and sample C was a sample of thermally denatured DNA. The DNA stain ethidium bromide becomes fluorescent when it intercalates into the double helical structure of intact native DNA. Hence, it can be used to identify the double-stranded DNA in FIG. 1. As the DNA is denatured, it becomes progressively single-stranded and the efficiency of staining with ethidium bromide decreases. However, there is still some residual staining of single-stranded calf thymus DNA, probably because there is still some ordering of the bases or even some regions which remain double-stranded to which ethidium bromide can bind. Therefore, the stain is still useful in detecting denatured DNA as well as intact DNA. In FIG. 1 it will be noted that the samples B and C are of much higher mobility than sample A through the gel indicating that the DNA after thermal denaturation and after electrical reduction has similar physical characteristics, showing a denaturation to the single stranded form which runs faster in this gel system. Similar results have been obtained using gold and platinum working electrodes.

EXAMPLE 2

Example 1 was repeated as before, but DNA samples were taken after 15 minutes, 3 hours and 22 hours treatment in the electrochemical cell in order to provide a time course of the denaturation of the DNA. During sampling from the cell, the potentiostat was switched to a dummy cell represented by a resistor. A gradual progressive denaturation of the DNA into the faster migrating form on the gel was observed. The gel pattern after 15 minutes (not shown) is interpreted to represent a mixture of partially and fully denatured DNA but no evidence of wholly native DNA was seen and, in later samples, the proportion of fully denatured DNA continued to increase.

EXAMPLE 3

In a number of runs at varying promoter concentrations and at a fixed DNA concentration of 20 μg/ml in the electrochemical cell and at an ionic strength of 15 mM to 150 mM the rate of DNA denaturation was found to be greatly accelerated by increasing the promoter concentration from 3 to 30 mg/ml. At the higher concentration, denaturation of the DNA was almost complete in 15 minutes only. In this example, the overwhelmingly predominant source of ionic strength is the promoter itself.

EXAMPLE 4

At a fixed promoter concentration of 3 mg/ml and at an ionic strength of 15 mM (derived essentially from the promoter) the rate of denaturation at various DNA concentrations was assessed. The results show that at 4 μg/ml DNA the denaturation time was reduced to under 0.5 hours (as assessed by the disappearance of the double-stranded DNA band on the electrophoresis gel).

The foregoing examples demonstrate that the ratio of DNA to the promoter methyl viologen affects the rapidity and completeness of the denaturation of the DNA. These examples were carried out at low ionic strength in distilled water. Repeating these examples at higher ionic strength, i.e., 10 to 250 mM NaCl, lengthened the denaturation time of the DNA in solution by electrical means. This is attributed to the additional stabilization that salt provides to the double helical structure of DNA.

The foregoing examples have also been repeated following exactly the procedure described above for calf thymus DNA with other whole genomic DNA samples from salmon testes DNA (Sigma No. D1626) and with human placental DNA (Sigma No. D7011). Exactly the same results were obtained on the agarose electrophoresis gel with these alternative DNA sources.

EXAMPLE 5

Figure 3:
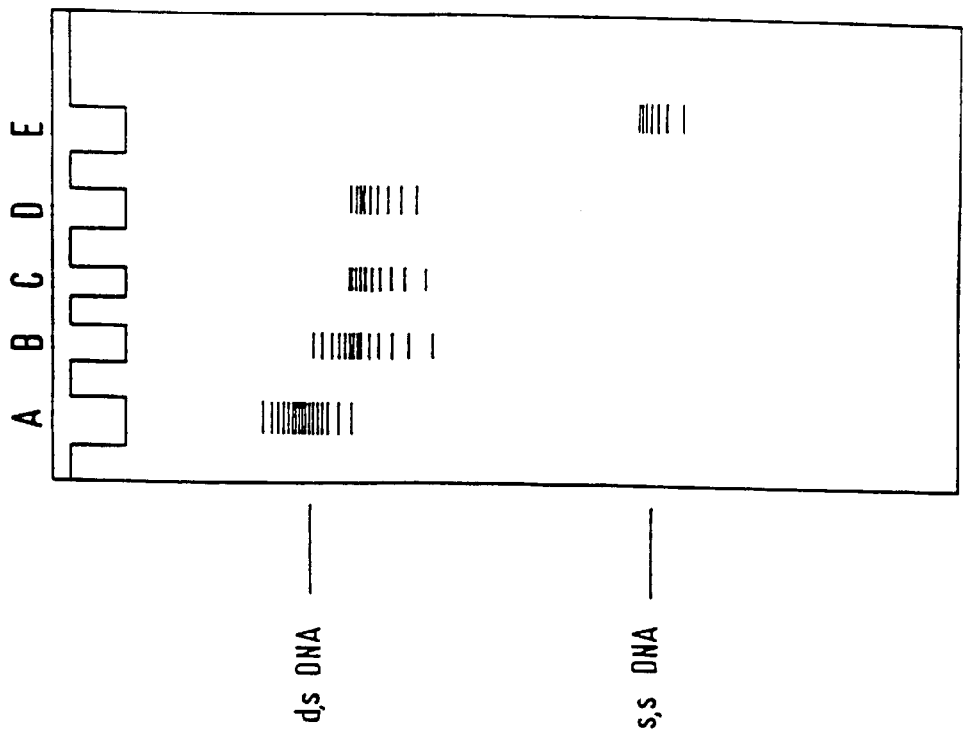
FIG. 3 is a diagram of an electrophoresis gel showing the electrical denaturation of calf thymus DNA in the absence of any promoter such as methyl viologen.

FIG. 3 shows the results of an electrical DNA denaturation carried out according to the methods described above but without the inclusion of the methyl viologen promoter. The ionic strength was less than 1 mM and the calf thymus DNA concentration was 70 μg/ml. The electrochemical cell was left for a total of 20 hours at ambient temperature (22° C.) with continuous gentle stirring at a potential of −(minus) 1.0 V on the working electrode. Samples were taken from the cell at 1 hour, 3 hours and 4 hours, as well as at the end of the procedure. During the sampling of the DNA solution from the cell, the potentiostat was switched to a dummy cell represented by a resistor in order to avoid current surges. The gel in FIG. 3 shows that denaturation of the calf thymus DNA to the single-stranded form does indeed occur in the absence of promoter, but the rate of the process was much slower than that observed with methyl viologen present. Track A is the starting material, Track B is after 1 hour, Track C after 3 hours, Track D after 4 hours and Track E after a total of 20 hours at −(minus) 1 V. Some limited denaturation of the DNA was observed within 1 hour, but considerable amounts of intact double stranded DNA were still visible after 4 hours and only disappeared after overnight incubation.

EXAMPLE 6

Figure 4:
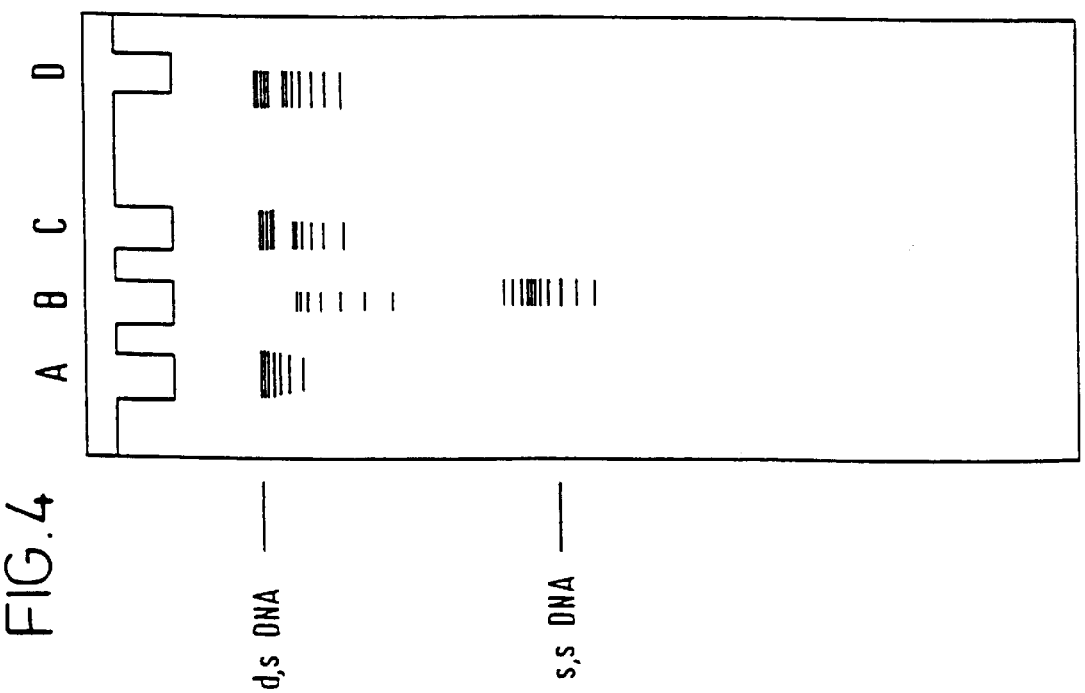
FIG. 4 is a diagram of an electrophoresis gel showing the renaturation of denatured calf thymus DNA.

FIG. 4 shows the results from a renaturation procedure in which electrically denatured DNA has been treated under the appropriate thermal and electrical condition to recover the original double-stranded DNA. To an electrochemical cell of the type shown in FIG. 1, 2.45 ml of distilled water was added to the working compartment and 0.2 ml of distilled water was added to the reference compartment. To the working compartment were added 250 μl of calf thymus DNA at 1 mg/ml in distilled water (pH not adjusted) and 100 Al of a solution of methyl viologen at 100 mg/ml in distilled water (pH adjusted to pH 7 with 0.1 M sodium hydroxide). The final DNA concentration in the solution was 90 μg/ml and the promoter 3.5 mg/ml. The ionic strength was approximately 15 mM derived essentially from the promoter. After gentle stirring of the contents of the cell with the magnetic stirring bar, a 100 μl sample was taken and stored on ice or frozen at −(minus) 20° C. The electrodes were positioned in the cell, as illustrated in FIG. 1, and a voltage of −(minus) 1 V. was applied to the working electrode. The contents of the cell were stirred gently with the magnetic stirring bar and the conversion of the DNA to the single-stranded form continued for 90 minutes at ambient temperature (22° C.). After 90 minutes the cell was switched to dummy and two 100 μl samples were taken, one sample was stored on ice, the second was incubated at 55° C. in a water bath after addition of 2 μl of 10 times concentrated "reannealing buffer" (final concentration 20 mM NaCl, 2 mM Tris HCl pH 8.7, 0.2 mM EDTA) for 25 hours. The voltage at the working electrode was reversed to +(plus) 1 V and treatment of the DNA solution in the electrochemical cell proceeded for a further 25 hours. After this second time period 100 μl of the DNA solution was removed from the cell and stored on ice. Each of the four 100 μl samples was mixed with 20 μl of gel loading buffer described above and stored on ice until required for electrophoresis.

FIG. 4 is an agarose gel run exactly as described above showing the four DNA samples;. A is the starting intact calf thymus material, B is the electrically denatured material, C is the electrically denatured and subsequently electrically renatured material, D is the electrically denatured material which was subsequently thermally renatured. It can be seen from the gel that both the electrically denatured thermally renatured and electrically denatured electrically renatured DNA returns to the original mobility of the double-stranded starting material.

EXAMPLE 7

This example illustrates that a bacteriophage genome can be electrically denatured to a single-stranded form in a manner analogous to the thermal method. Bacteriophage M13 (M13mp18RF1 Double-stranded form supplied by CP Laboratories, P.O. Box 22, Bishop's Stortford, Herts, UK) was employed. M13 is in circular form which can adopt a number of different coiled and supercoiled configurations. This leads to a complex set of bands on the agarose electrophoresis gel. Therefore, the gel pattern was simplified to a single band by subjecting M13 to a restriction digest with the enzyme BGL I, which has only one restriction site on the M13 genome. To one vial of M13 as supplied by CP Laboratories (containing 10 μg of M13 in 100 μl of buffer 10 mM Tris HCl pH 7.5 1 mM EDTA) 10 μl of "restriction buffer" was added (0.1 M Tris HCl pH 7.9, 0.01 M magnesium chloride, 0.05 M sodium chloride) and 6 μl of restriction enzyme (a stock at 8,000 U/ml supplied by CP Laboratories No. 143S). The solution was incubated at 37° C. in a water bath for 16 hours. To ensure the linearization was complete, 1 μl of the treated DNA was mixed with 3 μl of distilled water and 1 μl of gel loading buffer (described earlier) was run on a 1% agarose gel. If more than one band was seen after electrophoresis at 100 mA for 1 hour and subsequent staining, the DNA was redigested. Once linearity was determined, the M13 was precipitated by adding 125 μl of 1 M magnesium chloride, 25 μl of 3 M sodium acetate and 125 μl of absolute ethanol (AnalaR grade from BDH Ltd., Poole, UK). The mixture was frozen in dry ice for 20 minutes for 16 hours and the precipitate was collected by 15 minute centrifugation after thawing. The pellet was washed with 0.15 ml of 70% (v/v) ethanol and collected again by centrifugation. Finally, the pellet was dried under vacuum for 15 minutes and resuspended in 100 μl of distilled water.

The linearized M13 DNA was then subjected to both thermal and electrical denaturation. A series of tubes was set up. The series of 6 tubes contained 1 μl M13 DNA with 4 μl of distilled water. One tube was placed on ice, and the other tubes were heated for 2, 4, 6, 8, 10 minutes in a boiling water bath. After a brief period of centrifugation, the tubes were placed on ice (to prevent renaturation of the thermally denatured DNA). To each tube 1 μl of gel loading buffer was added. Before being loaded and subsequently run on a 1% agarose gel at 100 mA for 1 hour, each tube was briefly vortexed.

Figure 5:
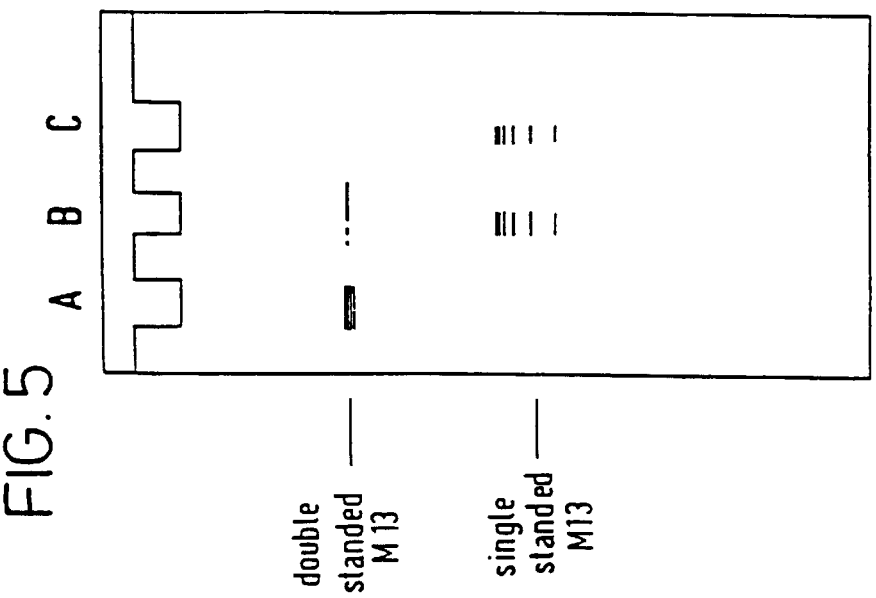
FIG. 5 is a drawing of an electrophoresis gel showing the time course of the thermal denaturation of linear double stranded DNA from the bacteriophage M13.

FIG. 5 shows the results from this thermal denaturation. Track A is the starting material (0 minutes at 100° C.), Track B is 2 minutes at 100° C., Track C is 6 minutes at 100° C.

It can be clearly seen from the gel that the intact double-stranded M13 rapidly disappears (within 4 minutes) from the gel as it denatures to single-stranded form which does not bind ethidium bromide stain with high efficiency. A faint smear remains on the gel with a higher mobility than native double-stranded DNA and this may be the very faintly stained single-stranded material.

For the electrical denaturation experiment, 920 μl of distilled water was added to an electrochemical cell as illustrated in FIG. 1. 30 μl of a 100 mg/ml solution of methyl viologen in distilled water was added along with 50 μl of linearized M13 to the electrochemical cell. The solution was then mixed gently using the stirring bar. A potential of –(minus) 1.0 V was applied to the working electrode. Samples (50 μl) were taken at timed intervals, and stored on ice until required. The DNA was precipitated by adding 5 μl of 1 M magnesium chloride, 25 μl of 3 M ammonium acetate and 125 μl of absolute (100%) ethanol to each sample. The precipitate was collected by freezing on dry ice and centrifuging as described above. The pellet was resuspended in 10 μl of distilled water and subjected to gel electrophoresis.

Figure 6:
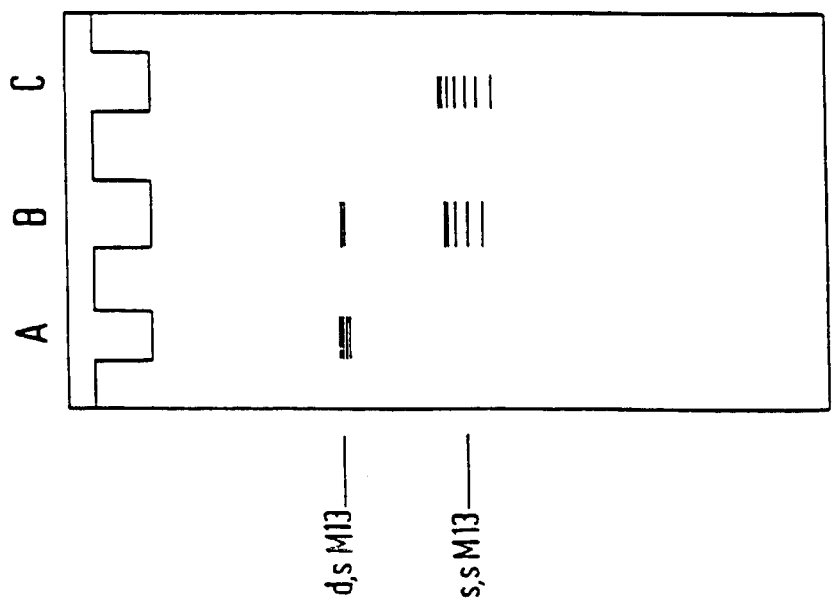
FIG. 6 is a drawing of an electrophoresis gel showing the time course of the electrical denaturation of linear M13 DNA.

FIG. 6 shows the time course of the electrical denaturation of M13. Track A is the starting material, Track B is after 5 minutes, Track C is after 15 minutes. The gel shows the loss of the double-stranded DNA structure which has disappeared by 15 minutes and the appearance of the faintly stained single-stranded smear.

EXAMPLE 8

Figure 7:
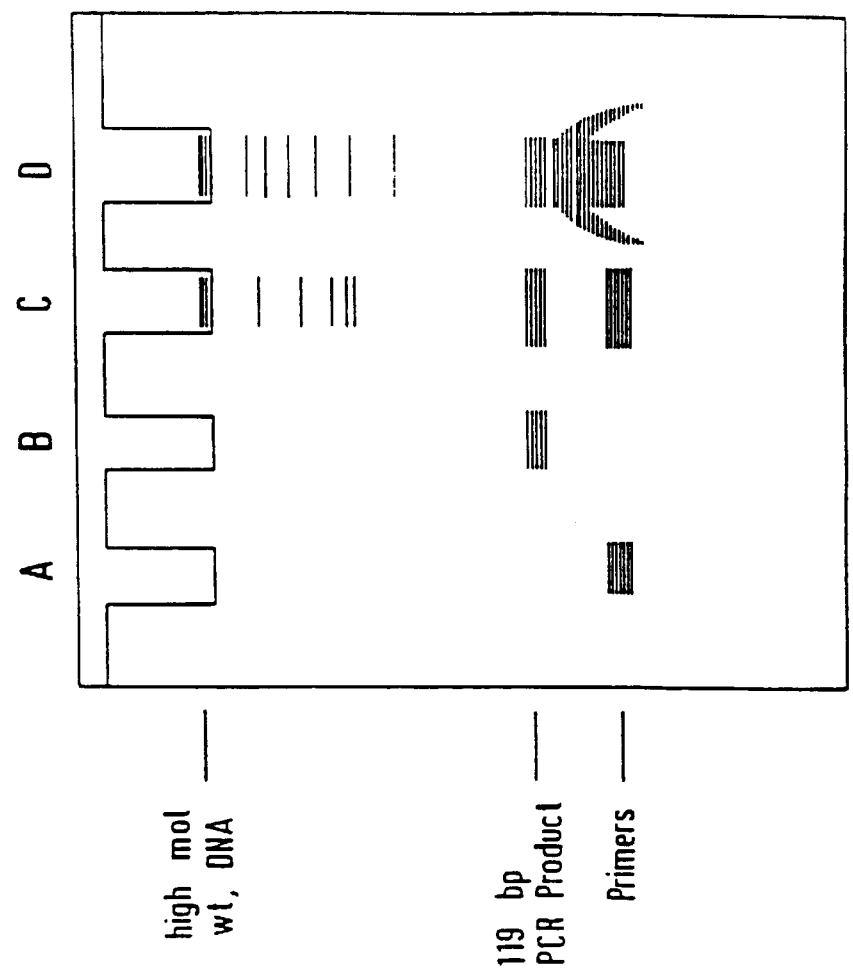
FIG. 7 is a drawing of an electrophoresis gel showing a comparison of a thermally-amplified segment of M13 with an equivalent electrically amplified segment of M13 in the presence of methyl viologen.

FIG. 7 shows the results from an electrochemical cell polymerase chain reaction (PCR) carried out in the presence of the promoter methyl viologen.

30 μl of a methyl viologen stock at 100 mg/ml (so the working concentration of methyl viologen was 3 mg/ml) and 50 μl of stock linear M13 were added to 920 μl distilled water (pH not adjusted) in the working compartment of the cell and gentle stirring achieved by a stirring bar. 200 μl of a 3 mg/ml solution of methyl viologen was added to the reference electrode compartment of the cell. All parts of this procedure were carried out at ambient temperature (22° C.). For the initial cycle of the polymerase chain reaction, a voltage of –(minus) 1 V. was applied for 7 minutes and it was observed that the reduced form of the promoter methyl viologen was produced and accumulated such that all the liquid became blue. Then the potentiostat was switched to dummy. The working/counter electrode was removed from the cell and the solution left stirring for 3 minutes and it was observed that the blue color rapidly disappeared during this period.

Reagents were then added to the cell, with the stirrer bar still stirring, namely 6 μl of primer (M13 Sequencing primer (–47) 24 mer 5'(CGCCAGGGTTTTCCCAGTCACGAC)3' supplied by ALTA Biosciences, University of Birmingham, UK, as a 5 μg lyophilized powder) at a final concentration of 78 pmol, 6 μl of reverse primer M13 Reverse Sequencing primer (–24)16mer 5'd(AACAGTCATGACCATTG)3' supplied as a 5 μg lyophilized powder) at a final concentration of 78 pmol, 13 μl of deoxynucleotide triphosphate mix (each DNTP present at a final concentration of 26 μm, supplied by Pharmacia Ltd., Midsummer Boulevard, Milton Keynes, UK), 4 μl buffer mix (at final concentration of 6.6 mM Tris HCl pH 8, 1 mM $MgCl_2$) and then 10 μl of Klenow DNA polymerase (supplied by CP Laboratories, as 5000 U/ml, and Northumbrian Biologicals Ltd., Cramlington, Northumberland, as 5000 U/ml). Excluding the promoter, the ionic strength was therefore about 20 mM. There was then a 7 minute incubation, with gentle stirring for the first 1 minute and no stirring for the next 6 minutes.

Then the working/counter electrode was replaced and the second cycle of the polymerase chain reaction started by −(minus) 1 V. being applied for 5 minutes and it was observed that the reduced form of the promoter methyl viologen was produced and accumulated such that all the liquid became blue. Then the potentiostat was switched to dummy. The working/counter electrode was removed from the cell and the solution left stirring for 3 minutes and it was observed that the blue color rapidly disappeared during this period. Reagents were then added to the cell, with the stirrer bar still stirring, i.e., 13 µl of deoxynucleotide triphosphate mix (details as above) and then 2.5 µl of Klenow DNA polymerase (details as above). There was then a 7 minute incubation with gentle stirring for the first 1 minute and no stirring for the next 6 minutes.

The second cycle was repeated as third to tenth cycles, omitting the adding of reagents at the end of the tenth cycle.

A sample was taken from the working compartment of the cell (750 µl) and it was split into sub-samples for ease of processing (3×250 µl), then to each tube was added 50 µl 1 M magnesium chloride, 98 µl 3 M sodium acetate and 500 µl 100% ethanol. The samples were frozen on dry ice for 20 minutes and then after thawing centrifuged for 15 minutes to obtain a pellet. The pellet was washed with 250 µl of 70% ethanol and centrifuged as described before. The pellet was dried under vacuum for 15 minutes and then the pellet in each tube was resuspended in 7 µl distilled water (pH not adjusted) and after extensive vortexing and leaving on ice, the contents of the 3 tubes pooled before running on a gel. 4 µl of gel loading buffer was added to the sample prior to running on a 12% polyacryamide electrophoresis gel (made according to the following recipe for three mini gels: 42 ml distilled $H_2O$, 8 ml TBE buffer (a stock of 500 ml distilled water containing 54 g. Trizma Base (Sigma T1503) 25 g. boric acid (Sigma B0252) 20 ml 0.5 M EDTA pH 8 (BDH 10093)), 24 µl 40% acrylamide solution (BDH 44354) 6 ml of 2% N'N' methylene bis acrylamide solution (BDH 44355), 400 µl 15% ammonium persulphate solution in distilled water (Sigma A7262), 100 µl TEMED (BDH 44308)).

In FIG. 7, lane A contains primers, these run faster on the gel than the thermally amplified 119 base pair fragment in lane B. Lanes C and D contain 5 µl and 15 µl, respectively, of electrically amplified product. In lanes C and D, high molecular weight M13 DNA is contained in the well, there is some smearing of DNA in the upper part of the gel, this is more pronounced in lane D. In both lanes, primers can be seen at the same mobility as in lane A, however, in lane D extensive "flaring" of the primers is observed. The amplified product can be seen in both lanes C and D at the same mobility as the thermally amplified sample in lane B.

EXAMPLE 9

Figure 8:
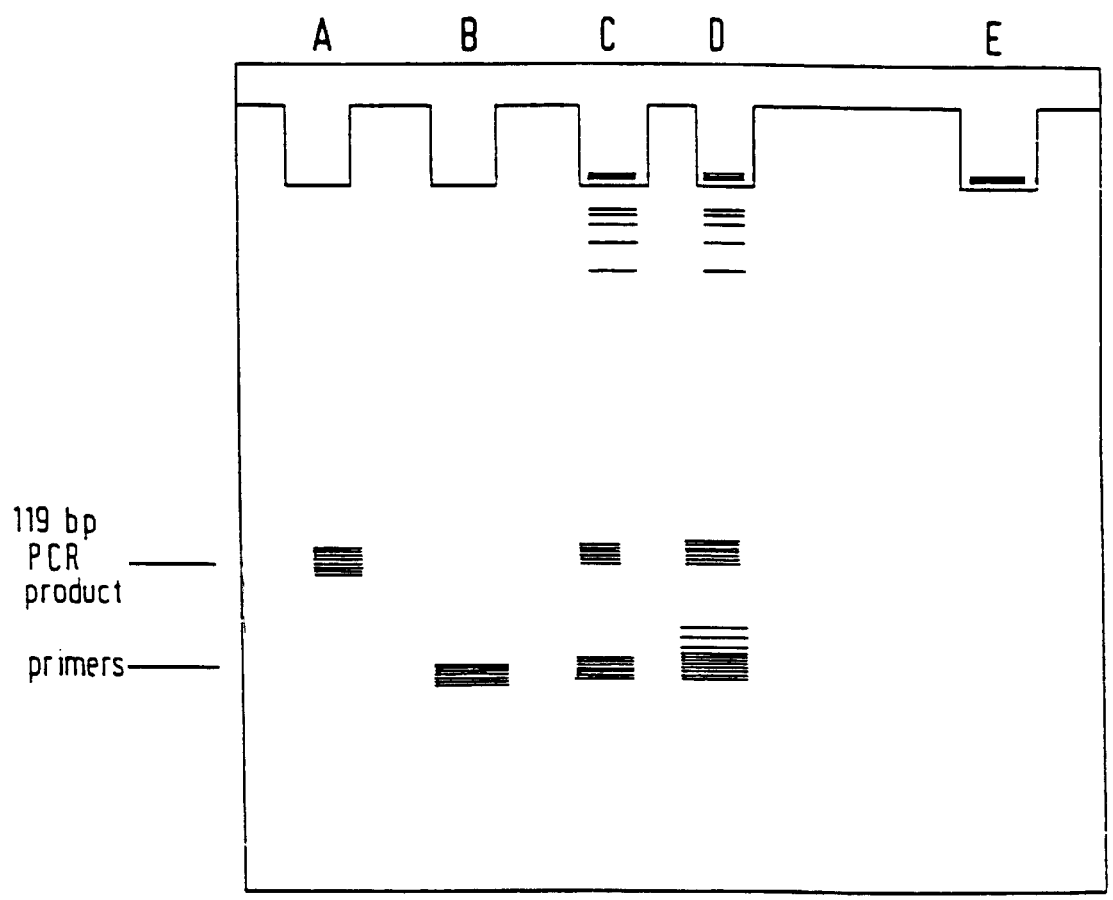
FIG. 8 is a drawing of an electrophoresis gel showing a comparison of a thermally-amplified segment of M13 with an equivalent electrically amplified segment in the absence of methyl viologen.

FIG. 8 shows the results from an electrochemical cell polymerase chain reaction (PCR) experiment carried out in the absence of promoter. The method used was essentially the same as for Example 8 with promoter described above except that no promoter is added to the cell and all additions of primer and reverse primer were of 3 µl each (not 6 µl as described above) and the experiment ran for 15 cycles.

In FIG. 8 lane A contains a thermally amplified 119 bp product, lane B primers, and lane E stock M13 that is confined to the well due to its high molecular weight. Lanes C and D contain the product of electrical amplification. The 119 base pair amplified region is clearly visible at the same mobility on the gel as the thermally amplified product. The primers in lanes C and D run at the same mobility as lane B.

The reduction of the amount of primers added in this experiment in comparison to the experiment illustrated in FIG. 7 reduces the flaring effect in the gel.

EXAMPLE 10

SK "Blue script" (Stratagene) is a circular 2,964 base pair vector. It contains a polylinker region which contains the M13 primer binding sites between which the target region of DNA amplified in Examples 8 and 9 is located.

Before use in this example, the blue script was linearized using restriction enzyme Xmn 1; this cuts at site 2645. Thus, to 80 µmoles of blue script, approximately 50 µg of DNA, 2.5 µl of −0.13 M -Tris buffer pH 7.9 containing 0.13 M magnesium chloride and 0.3 M sodium chloride and 8 µl of Xmn 1 restriction enzyme (Stratagene) was added. The mixture was incubated at 37° C. overnight. After phenol chloroform extraction and ethanol precipitation, the sample was resuspended to 50 µl in distilled water.

To the working compartment of the cell of FIG. 1 was added 1.2 ml of distilled water, and 30 µl of 100 mg/ml stock methyl viologen, 200 µl of this mixture was pipetted into the reference compartment. 50 µl (approximately 45 µg) of restriction digested SK blue script was added to the working compartment of the cell and the electrodes were placed in their respective compartments. Denaturing was conducted for 7 minutes at −1 V., and the working and counter-electrodes were removed from the cell. After 3 minutes stirring, to allow the reoxidation of the methyl viologen (a lagphase), the reagents listed below were added. The nucleic acid was allowed to anneal and extend for 5 minutes, the first minute with stirring and subsequent 4 minutes in the absence of stirring. The denaturing, lag phase and reagent addition, annealing and extending step were repeated for 10 cycles, but in cycles 2 through 10, the denaturation step was for 5 minutes.

Addition of reagents:

Cycle 1 4 µl of 1.65 M Tris buffer pH 8.7 containing 330 mM magnesium chloride

13 µl of dATP, dGTP, dTTP and dCTP at 10 mM each in distilled water (CHASE)

10 µl of Klenow DNA polymerase—as in Example B

3 µl of each of concentrated primer (2)

Cycle 2–4 and 6–10 5 µl of CHASE 2.5 µl of Klenow DNA polymerase

Figure 9:
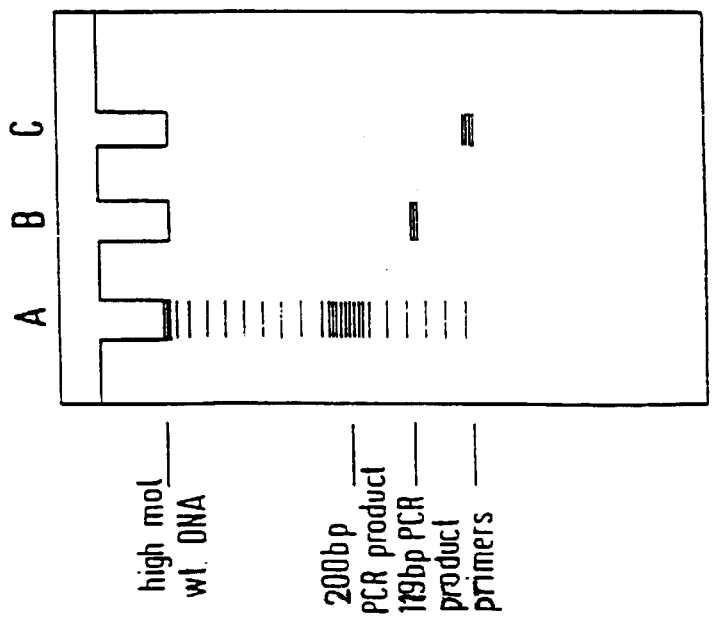
FIG. 9 is a drawing of an electrophoresis gel showing a fragment of "bluescript" DNA amplified using electrical PCR in the presence of methyl viologen.

After the 10 cycles were completed, the sample was divided into three and ethanol precipitated, dried and resuspended in 15 µl of distilled water. The sample was run on a 12% polyacrylamide gel at a constant current of 100 mA for 1 hour. The gel was stained with ethidium bromide. The gel is shown in FIG. 9.

Both the thermally amplified product of M13, a 119 bp band (run as a standard) and the primers can be clearly seen in lanes B and C, respectively. Due to the high concentration of DNA loaded onto lane A, the lane had high background, but a band of greater than 119 bp could be clearly seen. This band is the 200 bp amplified region of SK blue script.

EXAMPLE 11

The procedure of Example 10 was repeated except that further restriction digests were performed to produce 20 µg of linear 3000 base pair bluescript DNA using Xmn 1, and 15 µg of 450 base pair blue script DNA using Pvu 2 (Stratagene). The electrical PCR amplification process was performed in the absence of methyl viologen. A lag phase was not necessary and was omitted.

Figure 10:
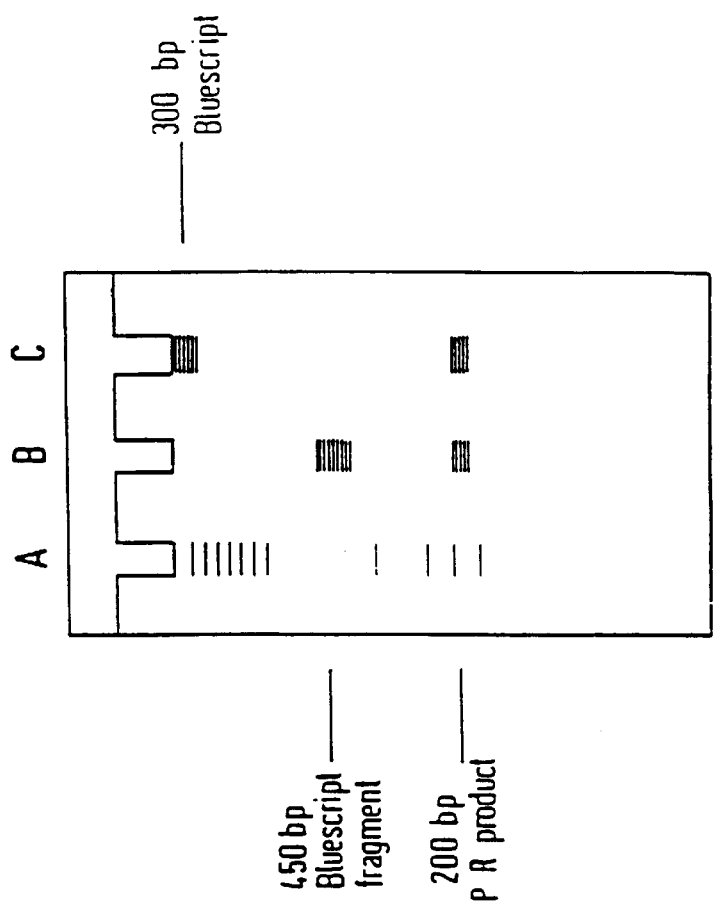
FIG. 10 is a drawing of an electrophoresis gel showing amplified fragments of two "bluescript" DNA's produced by electrical PCR in the absence of methyl viologen.

The polyacrylamide gel is shown in FIG. 10.

Lane A contains a "ladder marker," a set of known DNA sizes, which is used to gauge the molecular weight of experimental samples..

Lane B contains the 450 base pair electrically amplified "blue script" DNA. The template 450 base pair band can be clearly seen, as can an amplified band of 200 base pairs.

Lane C contains the 3000 base pair linear electrically amplified "blue script" DNA. The template DNA is confined to the well (as might be expected due to its 3000 base pair size) and an amplified band of 200 base pairs can clearly be seen.

Many modifications and variations of the invention as specifically described above are possible within the scope of the invention.

What is claimed is:

1. A process of identifying a gene sequence specific to a particular organism or specific to a hereditary disease in a sample which comprises:
    a) denaturing a sample of double-stranded nucleic acid by means of a voltage applied to the sample in a solution by means of an electrode so as to produce single-stranded denatured nucleic acid in the solution not bound to the electrode;
    b) hybridizing the denatured nucleic acid with an oligo-nucleotide probe for the sequence; and
    c) identifying the gene sequence by determining whether the hybridization has occurred.

2. A process as claimed in claim 1, wherein a potential of from −0.5 to −1.5 V is applied to the electrode with respect to the solution.

3. A process as claimed in claim 2, wherein the voltage is from −0.8 to −1.1 V.

4. A process as claimed in claim 1, further comprising the steps of:
    d) contacting the solution with the electrode, a reference electrode and a counter-electrode; and
    e) applying a voltage between the electrode and the counter-electrode so as to achieve a pre-selected voltage between the electrode and the reference electrode.

5. A process as claimed in claim 1, wherein the ionic strength of the solution is no more than 250 mM.

6. A process as claimed in claim 5, wherein the ionic strength is no more than 100 mM.

7. A process as claimed in claim 5, wherein the ionic strength is no more than 50 mM.

8. A process as claimed in claim 5, wherein the ionic strength is no more than 25 mM.

9. A process as claimed in claim 5, wherein the ionic strength is no more than 5 mM.

10. A process as claimed in claim 1, wherein the solution contains or the electrode has on its surface a promoter compound which assists the denaturalization.

11. A process as claimed in claim 10, wherein the compound is methyl viologen or a salt thereof.

12. A process as claimed in claim 1, wherein the electrode is constructed of carbon, gold or platinum.

13. A process as claimed in claim 1, carried out at a temperature less than the melting point of the double-stranded nucleic acid.

14. A process as claimed in claim 13, carried out at ambient temperatures.

15. A process as claimed in claim 1, carried out at a pH of from 3 to 10.

16. A process as claimed in claim 15, carried out at a neutral pH.

17. A process as claimed in claim 15, wherein the nucleic acid is dissolved in an aqueous solution containing a buffer whose nature and ionic strength are such as not to interfere with strand separation of the nucleic acid.

18. A process as claimed in claim 1, wherein the nucleic acid is DNA.

19. A process as claimed in claim 1, wherein the process is carried out as a denaturing step in a nucleic acid amplification procedure.

20. A process as claimed in claim 1, wherein the gene sequence is specific to a particular organism.

21. A process as claimed in claim 20, wherein the organism is a bacterium.

22. A process as claimed in claim 1, wherein the gene sequence is specific to a hereditary disease.

23. A process as claimed in claim 22, wherein the hereditary disease is sickle cell anemia.

* * * * *

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: M13 sequencing primer (-47)

<400> SEQUENCE: 1
cgccagggtt ttcccagtca cgac                                          24

<210> SEQ ID NO 2
<211> LENGTH: 17
<212> TYPE: DNA
<213> ORGANISM: Artificial Sequence
<220> FEATURE:
<223> OTHER INFORMATION: M13 reverse sequencing primer (-24)

<400> SEQUENCE: 2
aacagtcatg accattg                                                  17
```